(12) United States Patent
Nakagawa et al.

(10) Patent No.: US 8,506,159 B2
(45) Date of Patent: Aug. 13, 2013

(54) METHOD FOR DETECTING DEFECT IN MATERIAL AND SYSTEM FOR THE METHOD

(75) Inventors: Junichi Nakagawa, Tokyo (JP); Tadayuki Ito, Tokyo (JP); Tetsuo Nishiyama, Tokyo (JP); Masahiro Doki, Tokyo (JP); Kozo Saito, Lexington, KY (US); Belal Gharaibeh, Lexington, KY (US); Keng Hoo Chuah, Lexington, KY (US); Ahmad Salaimeh, Lexington, KY (US); Masahiro Yamamoto, Tokyo (JP); Tomoya Takeuchi, Tokyo (JP); Kazufumi Ito, Raleigh, NC (US); Huaxiong Huang, Markham (CA); Sean C. Bohun, Oshawa (CA)

(73) Assignee: Nippon Steel & Sumitomo Metal Corporation, Tokyo (JP)

( * ) Notice: Subject to any disclaimer, the term of this patent is extended or adjusted under 35 U.S.C. 154(b) by 0 days.

(21) Appl. No.: 13/060,658

(22) PCT Filed: Sep. 17, 2008

(86) PCT No.: PCT/US2008/076598
§ 371 (c)(1),
(2), (4) Date: May 19, 2011

(87) PCT Pub. No.: WO2010/033113
PCT Pub. Date: Mar. 25, 2010

(65) Prior Publication Data
US 2011/0249700 A1 Oct. 13, 2011

(51) Int. Cl.
*G01N 25/18* (2006.01)
*G01N 25/00* (2006.01)
*G01K 5/00* (2006.01)

(52) U.S. Cl.
USPC ............. 374/5; 374/121; 250/338.1; 250/340

(58) Field of Classification Search
USPC ............. 374/120, 121, 5, 4, 30, 29, 137, 166, 374/167, 110, 112, 115, 124, 45, 57, 100, 374/43, 44, 102, 103; 250/338.1, 240, 241.1, 250/363.01, 341.6, 363.02
See application file for complete search history.

(56) References Cited

U.S. PATENT DOCUMENTS 4,866,276 A * 9/1989 Leavens et al. ............ 250/341.6
4,988,210 A * 1/1991 Koshihara et al. ................ 374/5
(Continued)

FOREIGN PATENT DOCUMENTS

AT 501845 A2 * 11/2006
CN 1547666 A 11/2004
(Continued)

OTHER PUBLICATIONS

Japanese Office Action, dated Oct. 4, 2011, for Japanese Application No. 2011-517394 with partial English Summary.
(Continued)

*Primary Examiner* — Gail Verbitsky
(74) *Attorney, Agent, or Firm* — Birch, Stewart, Kolasch & Birch, LLP

(57) ABSTRACT

A defect on the surface or in the surface layer of a moving material can be detected by using a method comprising steps of: heating the surface of the material, obtaining thermal image data of the surface of the material using an infrared thermography camera while the surface of the material is being heated up at the heating step or being cooled down after heating, and detecting the defect by calculating Laplacian with respect to temperature of the surface represented by the thermal image data. When the thermal image data is obtained while the material is being heated up, a heating device and the camera is arranged so that thermal energy emitted from the heating device is reflected by the material to come into the camera.

15 Claims, 19 Drawing Sheets

(56) References Cited

U.S. PATENT DOCUMENTS

| | | | |
|---|---|---|---|
| 5,131,758 A * | 7/1992 | Heyman et al. | 374/5 |
| 5,292,195 A * | 3/1994 | Crisman, Jr. | 374/4 |
| 5,396,068 A * | 3/1995 | Bethea | 250/330 |
| 5,711,603 A * | 1/1998 | Ringermacher et al. | 374/5 |
| 5,716,133 A * | 2/1998 | Hosokawa et al. | 374/121 |
| 6,000,844 A * | 12/1999 | Cramer et al. | 374/5 |
| 6,236,044 B1 | 5/2001 | Chou et al. | |
| 6,420,705 B2 | 7/2002 | Chou et al. | |
| 6,461,035 B2 * | 10/2002 | Meinlschmidt et al. | 374/5 |
| 6,840,666 B2 * | 1/2005 | Enachescu et al. | 374/5 |
| 7,018,094 B1 * | 3/2006 | Bates | 374/121 |
| 7,083,327 B1 * | 8/2006 | Shepard | 374/46 |
| 7,401,976 B1 * | 7/2008 | Schlagheck et al. | 374/5 |
| 7,553,070 B2 * | 6/2009 | Kollgaard et al. | 374/5 |
| 7,568,832 B2 * | 8/2009 | Safai et al. | 374/10 |
| 8,097,857 B2 | 1/2012 | Cochran et al. | |
| 8,220,991 B2 * | 7/2012 | Safai et al. | 374/163 |
| 2001/0054693 A1 | 12/2001 | Chou et al. | |
| 2003/0193987 A1 * | 10/2003 | Zalameda et al. | 374/5 |
| 2005/0251039 A1 * | 11/2005 | Chalana et al. | 600/437 |
| 2006/0289766 A1 | 12/2006 | DiMarzio et al. | |
| 2009/0245321 A1 * | 10/2009 | Ringermacher et al. | 374/5 |
| 2010/0033565 A1 * | 2/2010 | Benzerrouk et al. | 348/125 |

FOREIGN PATENT DOCUMENTS

| | | |
|---|---|---|
| EP | 0 333 100 A2 | 9/1989 |
| EP | 0 985 924 A1 | 3/2000 |
| EP | 1852697 A1 | 11/2007 |
| JP | 62-126339 A | 6/1987 |
| JP | 1-239443 A | 9/1989 |
| JP | 11-83773 A | 3/1999 |
| JP | 2000-65759 A | 3/2000 |
| JP | 2001-50921 A | 2/2001 |
| JP | 2004-20336 A | 1/2004 |
| JP | 2004-219177 A | 8/2004 |
| JP | 2006-90801 A | 4/2006 |
| JP | 2007-327755 A | 12/2007 |
| WO | WO 2007/147158 A2 | 12/2007 |

OTHER PUBLICATIONS

Cramer at al., "Thermographic Imaging of Cracks in Thin Metal Sheets", SPIE Thermosense XIV, vol. 1682, XP002530355, pp. 162-170. Apr. 24, 1992.

International Search Report, dated Jun. 18, 2009, issued in PCT/US2008/076598.

Plotnikov et al., "Visualization of subsurface defects in composites using a focal plane array infrared camera", SPIE Conference on Thermosense XXI, vol. 3700, XP-002530356, pp. 26-31, Apr. 1999.

CN Office Action dated Jun. 29, 2012 for Appl. No. 200880131156.6 w/ English translation.

KR Office Action dated Aug. 10, 2012 for Appl. No. 10-2011-7008587 w/ partial English translation.

Taiwanese Office Action dated Jan. 22, 2013 for Taiwanese Application No. 098130207 with English translation.

* cited by examiner

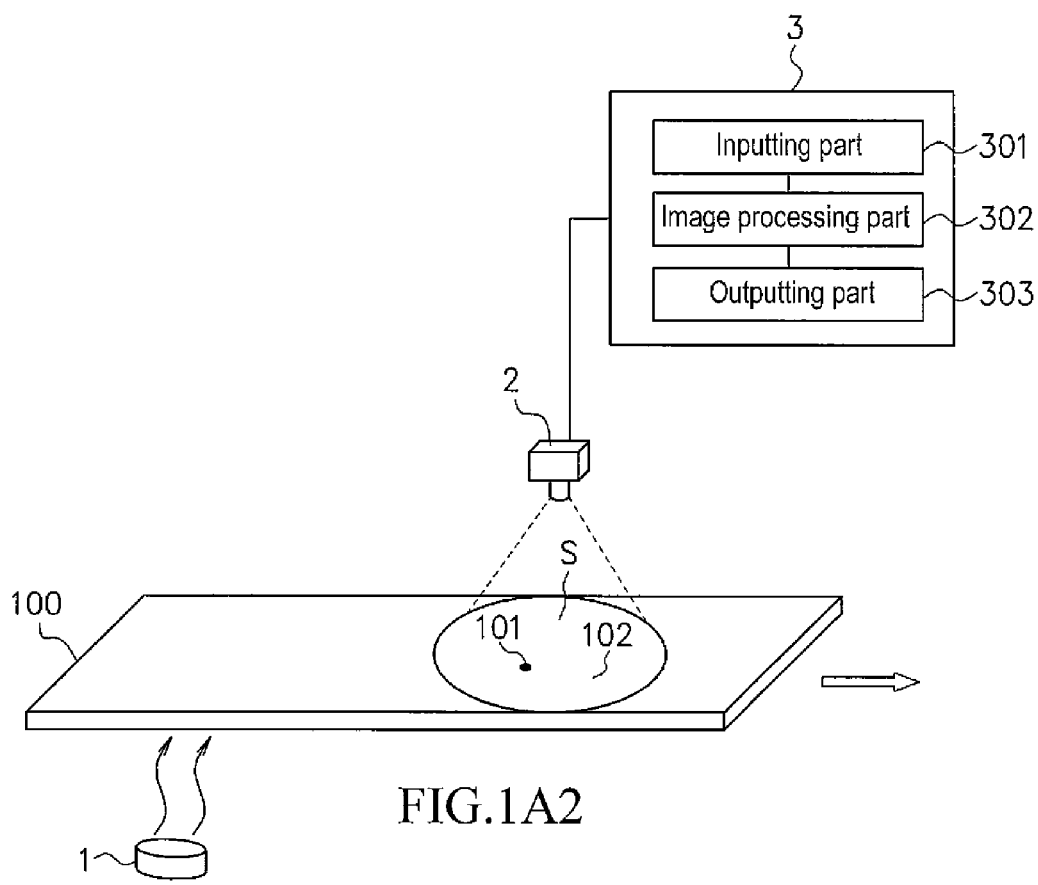
FIG.1A2
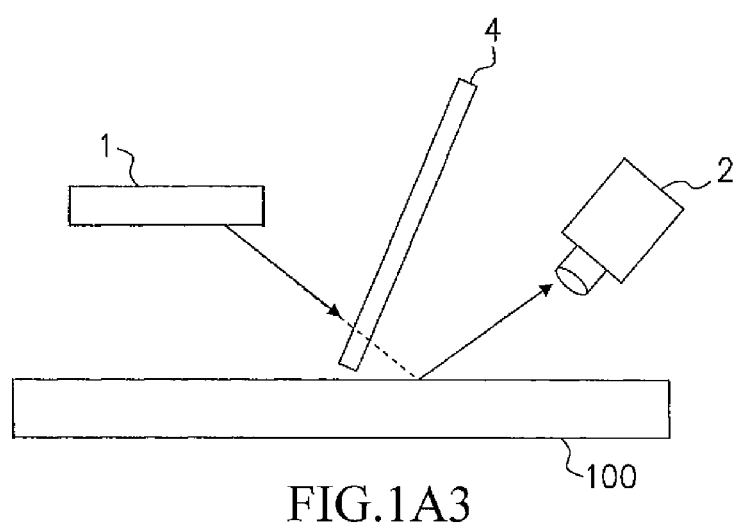
FIG.1A3

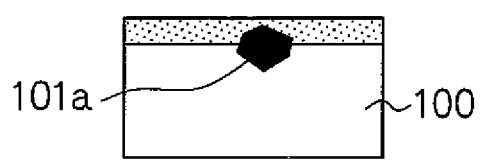
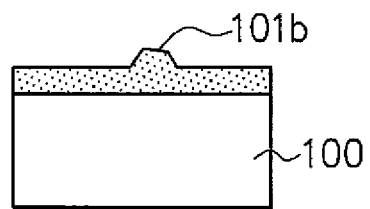
FIG.3A  FIG.3B
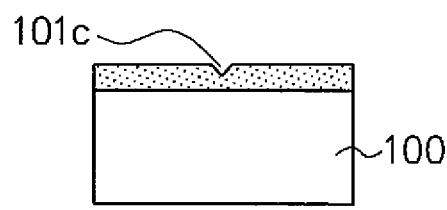
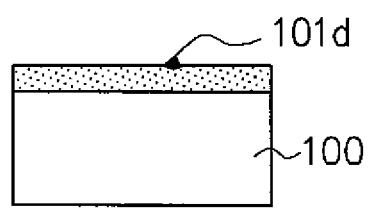
FIG.3C  FIG.3D
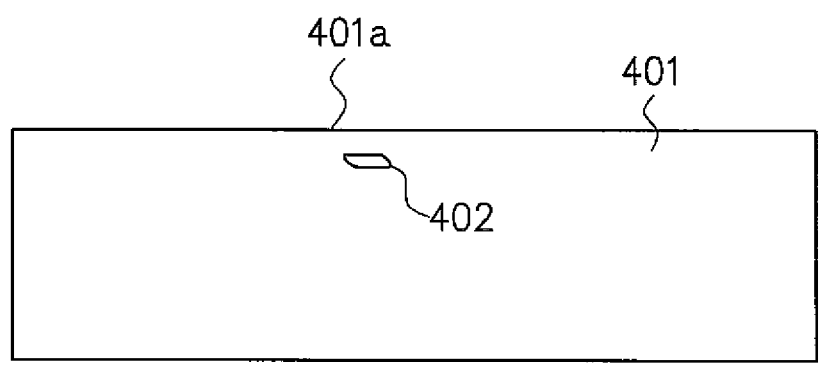
FIG.4

METHOD FOR DETECTING DEFECT IN MATERIAL AND SYSTEM FOR THE METHOD

FIELD OF THE INVENTION

The present invention relates to a method for detecting a defect in a material and a system for the method suitable for detecting a defect on the surface and/or in the surface layer of the material.

DESCRIPTION OF THE RELATED ART

In the case of steel sheet material, the steel sheet may have many types of defects such as a dent by the roll, a dross flaw formed by embedding a dross from hot dip galvanizing in the galvanized layer, blowholes scattered inside the steel sheet which are formed when argon gas is trapped in the cast metal during the casting process, or a surface defect caused by non-uniformity in the thickness of the galvanized layer.

Among these defects on a steel sheet, a defect of a difference in color from the other normal portions has been detected by operator's visual check.

As shown in JP 2004-219177A, defect detecting technology is known, which can detect a defect of a steel sheet based on sheet surface image data taken by CCD camera.

However, the production line speed has to be reduced when an operator does a visual check and also the accuracy of the visual check by the operator depends on the person. Recently, detection of defects of which size is too small to be visually detected has been required as high level of quality control has been demanded.

Furthermore, the CCD camera method of visually checking the surface of a steel sheet does not have a high ability for detecting a defect located in the surface layer (not on the surface) since such a defect is often difficult to be visually recognized from outside.

BRIEF SUMMARY OF THE INVENTION

The present invention has been conceived based on consideration of the above problem. An object of the present invention is therefore to provide a method and system for detecting a defect both on the surface and in the surface layer of a material, such as a steel sheet, with high accuracy even if the material is moving or being transported.

In the present invention, a defect of a material can be detected using a method for detecting a defect both on the surface and in the surface layer of a material including the steps of: heating the surface of the material, obtaining thermal image data of the surface of the material using an infrared thermography camera while the material is being heated up at the heating step or being cooled down after heating, and detecting the defect by calculating Laplacian with respect to the temperature of the surface represented by the thermal image data. The method can be performed by the following system. A system for detecting a defect both on the surface and in the surface layer of a material includes: a heating device for heating the surface of the material, an infra-red thermography camera for obtaining thermal image data of the surface of the material while the material is being heated up at the heating step or being cooled down after heating, and a detecting device for detecting the defect by calculating Laplacian with respect to the temperature of the surface represented by the thermal image data.

According to the present invention, the detection of a defect is carried out by: heating the surface of the material, obtaining thermal image data of the surface of the material using an infrared thermography camera while the material is being heated up at the heating step or being cooled down after being heated up, and detecting the defect by calculating Laplacian with respect to the temperature of the surface represented by the thermal image data. This makes it possible to detect the defect both on the surface and in the surface layer of the material with high accuracy even if the material is moving or being transported.

BRIEF DESCRIPTION OF THE DRAWINGS

FIG. 1A2 shows a camera in a different setup direction and location relative to the steel sheet surface. FIG. 1A3 shows an alternative way to use a heat shielding member.

FIGS. 3A, 3B, 3C and 3D show a type of defect to be detected in the present invention.

FIG. 4 is an explanatory diagram for explaining a nondestructive inspection using an infrared thermography camera.

DETAILED DESCRIPTION OF THE INVENTION

Figure 1A:
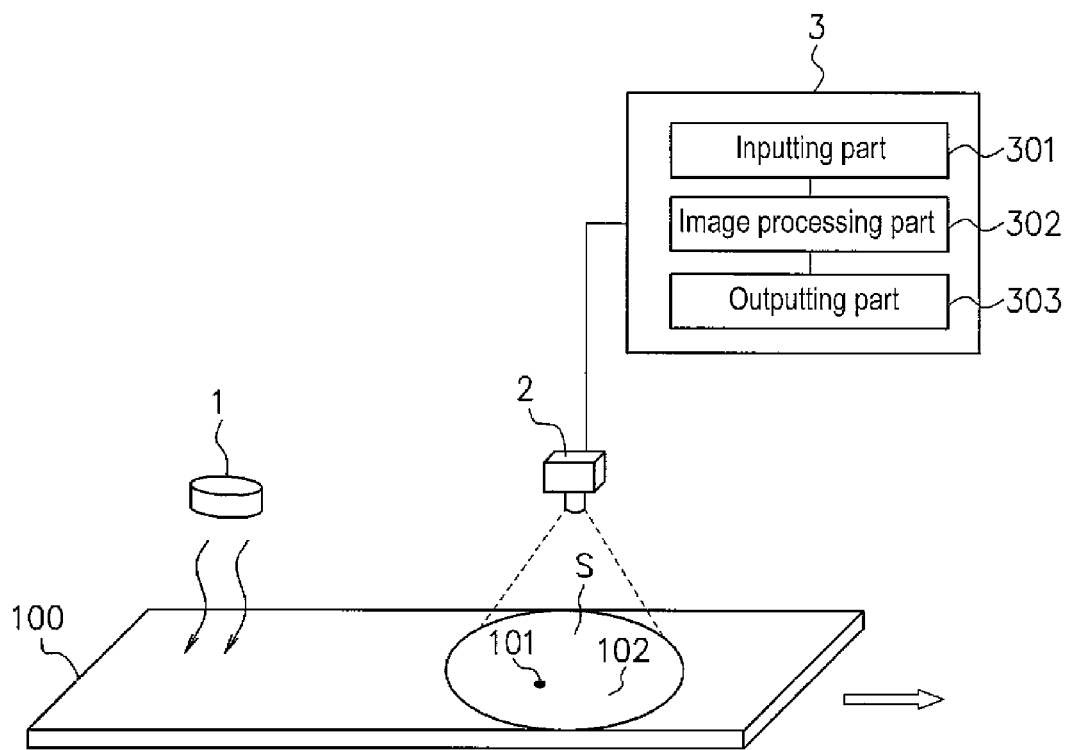
FIG. 1A and FIG. 1B show a rough configuration of the system for detecting a defect of a steel sheet in one embodiment of the present invention, where the detection is made while the material to be inspected is cooled down after being heated up.

The present invention is more specifically set forth in the case of a steel sheet material in the following description with reference to the appended figures. As shown in FIG. 1A and FIG. 1C, the defect detecting system of the present invention has a heating device 1, an infrared thermography camera 2 and a detecting device 3, which detects a defect on the surface and/or in the surface layer (referred to as simply defect 101) of a steel sheet 100 (e.g., several mm in thickness).

A defect 101, the object to be detected in the invention, is described below with reference to FIGS. 3A-3D. There are many types of defects on the surface/in the surface layer of the steel sheet 100 and the shape of the defect can be, for example, as sort of scattered-sand, willow-leaf or spot.

A defect 101*a* in FIG. 3A is a defect caused by embedding some foreign material in the surface layer of the steel sheet 100, that is, e.g., a dross flaw formed by embedding a dross from hot dip galvanizing into the galvanized layer, or caused by formation of a void, that is, e.g., blowholes scattered inside the steel sheet which are formed when argon gas is trapped in the cast metal during the casting process and the gas trapped portion is rolled out during the rolling process. In this type of defect, thermal conductivity of the defect (foreign material/void) 101*a* is lower than that of a steel sheet per se. Consequently, the surface of steel sheet at the position of the defect 101*a* (the surface adjacent to the defect) can be more rapidly heated up or cooled down compared with the normal surface portion of the steel sheet.

A defect 101*b* in FIG. 3B is a minute raised convex portion formed on the surface of the steel sheet 100. A locally much thicker galvanized layer is one example of this defect. In this type of defect, the raised convex portion 101*b* has a larger surface area, which makes the raised convex portion 101*b* be more rapidly heated up or cooled down compared with other normal surface portions of the steel sheet. Also because of the shape of the defect, the amount of heat radiation from the area of the raised convex portion 101*b* is larger than that from the same size area of other normal surface portions of the steel sheet.

A defect 101*c* in FIG. 3C is a minute sharp dent formed on the surface of the steel sheet 100. This defect is often formed by pressing some foreign material attached on the surface of a roll against the steel sheet. Because of the shape of the defect, the amount of heat radiation from the area of the sharp dent 101*c* is larger than that from the same size area of other normal surface portions of the steel sheet. This makes the area of the minute sharp dent 101*c* be more rapidly heated up or cooled down compared with other normal surface portions of the steel sheet.

A defect 101*d* in FIG. 3D is a foreign material such as dust attached on the surface of the steel sheet. In this type of defect, the radiation rate of the foreign material is higher than that of the steel sheet. Consequently, the amount of heat radiation from the defect 101*d* is larger than that from the same size area of other normal surface portions of the steel sheet. This makes the area of the foreign material 101*d* be more rapidly heated up or cooled down compared with other normal surface portions of the steel sheet.

The present invention has been made based on the fact inventors found that when Laplacian $\Delta_{xy}T$ was obtained with respect to the temperature of the surface represented by the thermal image data taken using an infra-red thermography camera, absolute value of the Laplacian $\Delta_{xy}T$ becomes larger at the position of the defect 101 compared with other normal surface portion of the steel sheet and also the type of the defect can be determined based on whether the value of Laplacian $\Delta_{xy}T$ is positive or negative.

FIG. 1A shows a rough configuration of the system for detecting a defect of a steel sheet of one embodiment of the present invention. FIG. 1C shows a rough configuration of the system for detecting a defect of a steel sheet of another embodiment of the present invention. In FIG. 1A and FIG. 1C, a heating device 1 heats up the surface of the steel sheet 100 on an inspection line. It is preferable that the temperature of the steel sheet is less than 100° C. (more preferably about 60° C.) in order to set the temperature of the steel sheet 100 higher than room temperature and avoid any effect on the quality of the steel sheet. A steel sheet on an inspection line is transported in the arrow direction at a predetermined line speed ranging from 0 to about 300 mpm.

Figure 1B:
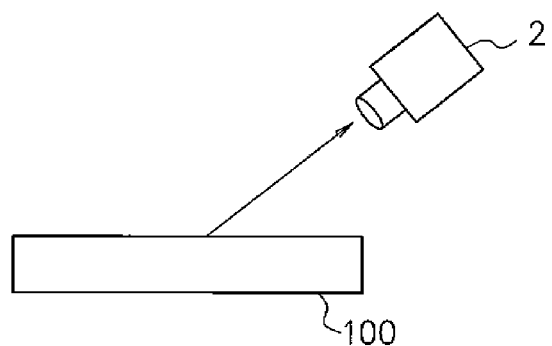
Figure 1C:
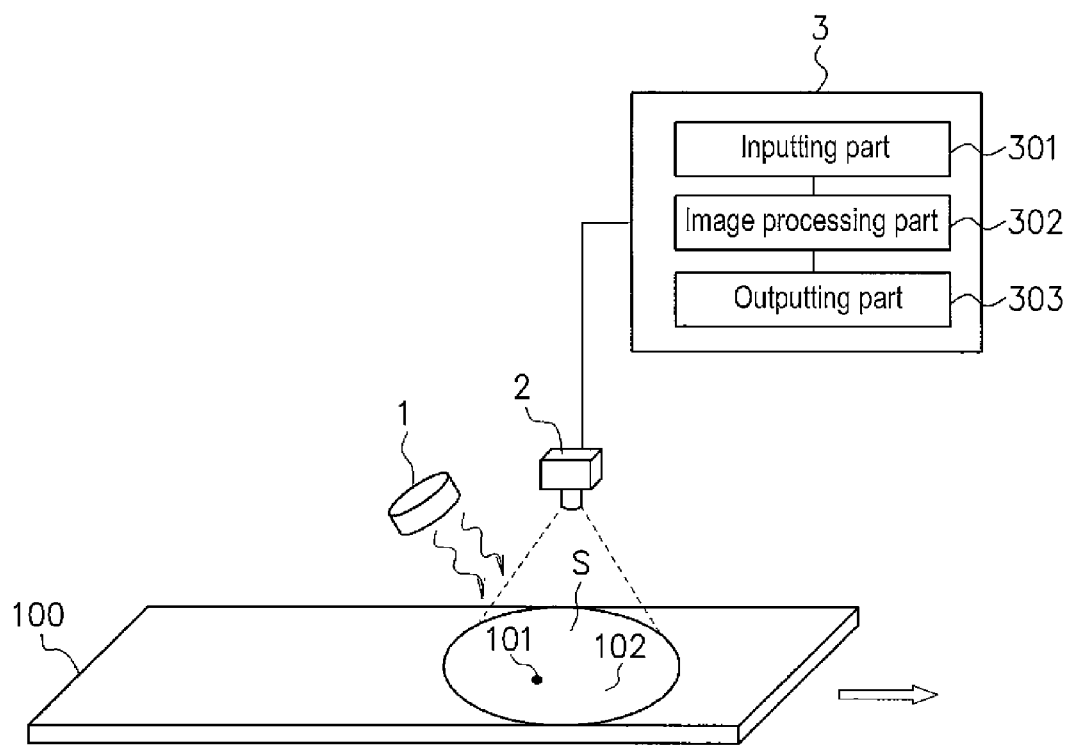
FIG. 1C shows a rough configuration of the system for detecting a defect of a steel sheet in another embodiment of the present invention, where the detection is made while the material to be inspected is being heated up.

FIG. 1A and FIG. 1B illustrate a system suitable for detecting defects while a steel sheet is being cooled down. In FIG. 1A, an infrared thermography camera 2 is located downstream from a heating device 1. The steel sheet is heated upstream by the heating device 1 and the surface area of the steel sheet is thermographed downstream at an inspection area S to obtain two-dimensional thermal image data of the inspection area S. Thermal image means an image representing a distribution of the amount of heat radiation radiated from the surface of the steel sheet 100 of an object to be inspected, in other words, an image representing a surface temperature distribution. The infrared thermography camera 2 has an image pick-up portion with an infrared sensor and a signal processing part, which can provide thermal image data by converting temperature information of each pixel into color information.

In the process of obtaining thermal image data of the inspection area S using the infrared thermography camera 2, it is necessary to avoid thermal energy emitted by the heating device 1 from coming into the infrared thermography camera 2 directly or by being reflected by the surface of the steel sheet 100. For this reason, the heating device 1 and the thermography camera 2 are placed so as to have sufficient distance between them. In the case where it is difficult to have sufficient distance therebetween because of limited space, it is an alternative way to have a heat shielding member 4 therebetween as shown in FIG. 1A3 to avoid thermal energy emitted by the heating device 1 from coming into the infrared thermography camera 2 by being reflected by the surface of the steel sheet 100. Needless to say, the heat shielding member 4 is arranged so as not to block the field of view of the thermography camera 2. It is preferable to have such an arrangement in order to avoid thermal energy emitted by the heating device 1 from coming into the infrared thermography camera 2 even if the heating device 1 is to be turned off after heating the steel sheet 100, since some thermal energy from the remaining heat of the turned off heating device could come into the camera.

A camera 2 in FIG. 1A, FIG. 1A2 and a camera 2 in FIG. 1B are different in setup direction (optical axis direction of the optical system of the camera) and location relative to the steel sheet surface. A variety of directions and locations of the camera and heating device 1 can be used in the invention.

In the case where defect detecting is made while a steel sheet is heated up (described later), also a variety of directions and locations can be used, as long as the heating device 1 and the thermography camera 2 are arranged so that the thermal energy emitted by the heating device 1 can come into the camera after being reflected by the surface of the steel sheet.

In an infrared thermography camera 2, frame rate and integration time are set so as to fit the production line speed. In a commercially available infrared thermography camera, the integration time is in the order of 0.01 ms. This means there is only 0.025 mm of slippage when the steel sheet runs at 150 mpm, which leads to only 10% or less with respect to a pixel having a size of 0.25 mm or more. In other words, the quality of the image is almost not degraded.

A detecting device 3 with a personal computer calculates Laplacian $\Delta_{xy}T$ based on a surface temperature represented by the thermal image data obtained by the infrared thermography camera to detect a defect 101 and determine the type of the defect. As described before, absolute value of Laplacian $\Delta_{xy}T$ at the position of the defect 101 is larger than that at the position 102 of a normal surface portion of the steel sheet and the type of the defect can be determined based on whether the value of Laplacian $\Delta_{xy}T$ is positive or negative. Therefore, if there is a defect in the inspection area S, the absolute value of Laplacian $\Delta_{xy}T$ of the defect position shows a larger value compared with that of a normal surface portion of the steel sheet, and the type of the defect is determined by whether the value is positive or negative.

The detecting device 3 includes an inputting part 301 into which thermal image data obtained by the infrared thermography camera 2 is input.

Figure 2A:
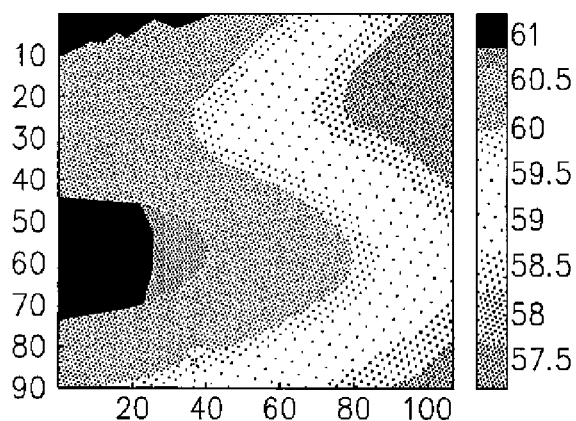
FIGS. 2A, 2B and 2C are schematic diagrams to illustrate an example of the image data processing performed in the image processing part of the detecting device.
Figure 2B:
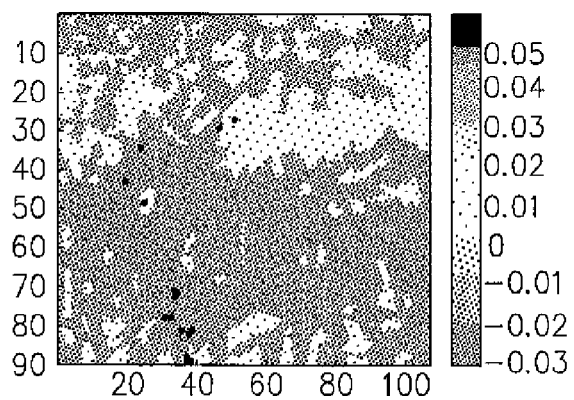
Figure 2C:
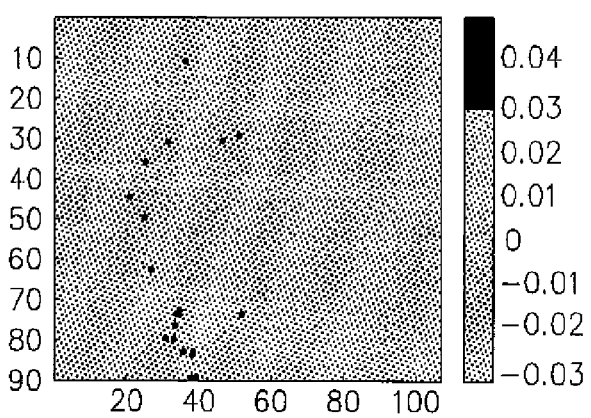

An image processing part 302 in the detecting device 3 is for processing the thermal image data input into the inputting part 301 in accordance with a predetermined image data processing procedure. FIGS. 2A, 2B and 2C are schematic diagrams to illustrate an example of the image data processing performed in the image processing part 302 of the detecting device 3. FIG. 2A shows thermal image data input into the inputting part 301. FIG. 2B shows Laplacian-processed thermal image data where the temperature is converted into Laplacian value. FIG. 2C shows a binarized image of the thermal image data of Laplacian value. Laplacian processing is performed in order to reduce a disturbance in the thermal image data (FIG. 2A) provided by temperature irregularity, and also to detect the heat balance taking place at the surface and surface layer of the steel sheet 100 as described later. A surface layer is defined as a part very close to the surface of the material and experientially about one fourth of the thickness region from the surface can be regarded as the surface layer in the case of a 1-2 mm thick steel sheet.

Since the absolute value of Laplacian $\Delta_{xy}T$ at the position of the defect 101 is detected larger in the inspection area S, it can be said that Laplacian processing can provide the image where the defect 101 is extracted (see the black colored portion in FIG. 2C). Also the type of the defect 101 can be determined based on whether the value of Laplacian $\Delta_{xy}T$ is positive or negative.

An outputting part 303 in the detecting device 3 is for outputting the thermal image data processed by the image processing part 302 to display on a monitor screen (not shown).

The method of the invention for detecting a defect on the surface and/or in the surface layer of a steel sheet is described in detail below.

An infrared thermography camera can be used to detect an inside defect 402 (e.g., captured foreign material or formation of void) located inside the object-to-be-inspected 401 as shown in FIG. 4. As thermal conductivity of the object-to-be-inspected 401 and that of the defect 402 are generally different, the amount of heat radiation from the surface at the position of the object-to-be-inspected 401 is different from that of the defect 402. Consequently, the defect 402 inside the object-to-be-inspected 401 can be detected by measuring a distribution of the heat radiation amount with time over the surface of the object-to-be-inspected 401.

If the thermal conductivity of the object 401 and that of the defect 402 are greatly different from each other, it is possible to detect the defect 402 with high accuracy. If the object 401 and the defect 402 have the same or almost the same thermal conductivity, for example, in the case of FIG. 3B and FIG. 3C where there is no difference between the object and the defect, this method cannot be used.

This method detects an abnormality of temperature in the defect position based on the heat radiation amount distribution. The distribution is, however, affected by the heat diffusion in two dimensions (x-y directions) of the surface of the object. Therefore the heat radiation amount at the defect position is attenuated, which lowers the accuracy of detecting the defect position.

In the defect detecting method of the present invention, Laplacian processing is performed in addition to the use of distribution of heat radiation amount of the object (steel sheet 100). As described before, the absolute value of Laplacian $\Delta_{xy}T$ at the position of the defect 101 is detected larger than that at the position 102 of a normal surface portion of the steel sheet. This invention is based on the idea that if there is a defect 101 in an inspection area S, the absolute value of Laplacian $\Delta_{xy}T$ at the position of the defect 101 should be recognized larger than that of other normal surface portions.

Figure 5:
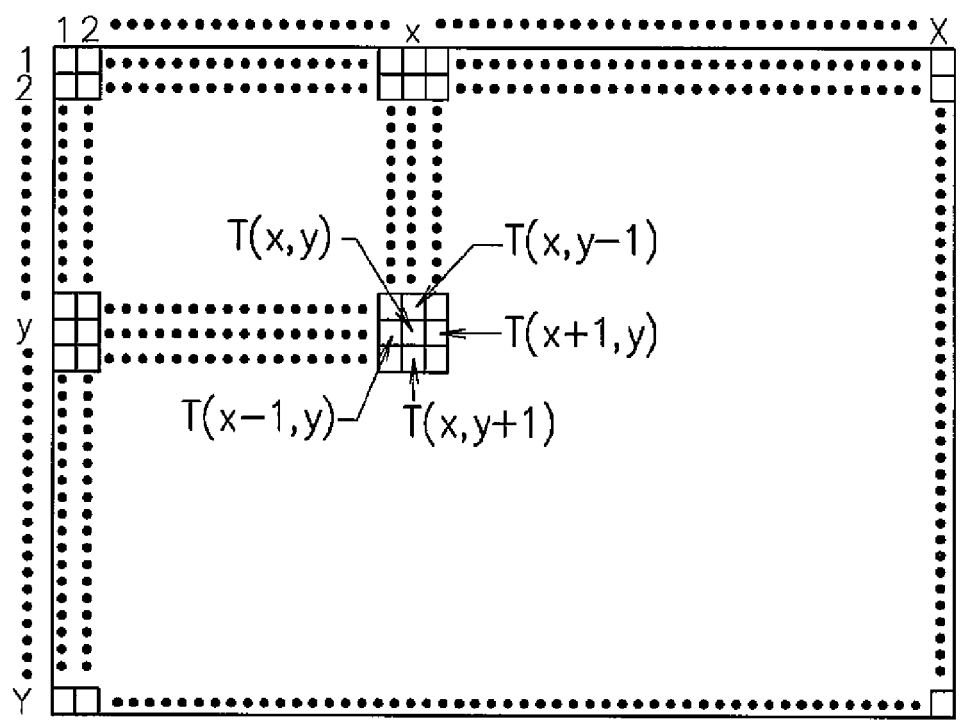
FIG. 5 is an explanatory diagram explaining the relationship between pixels for calculating Laplacian.

A Laplacian $\Delta_{xy}T$ with respect to a pixel is represented by an expression (1) below. As shown in FIG. 5, the right-hand side of the expression (1) can be calculated using a surface temperature T(x, y) of the pixel based on thermal image data obtained by the infrared thermography camera and the temperatures of each the of pixels located respectively above, below, right side of and left side of the pixel; i.e., T(x+1, y), T(x, y+1), T(x−1, y), T(x, y−1), where h is the size of the pixel. In the above, Laplacian is calculated with respect to each single pixel. Laplacian can also be calculated with respect to each block consisting of a plurality of pixels (e.g., 2-pixel by 2-pixel).

$$\Delta_{xy}T = \frac{1}{4h^2}\{T(x+1, y) + T(x-1, y) + T(x, y+1) + T(x, y-1) - 4T(x, y)\}. \quad (1)$$

As a heat migration phenomenon inside the steel sheet 100 meets a nonsteady-state three-dimensional heat conduction equation, Laplacian $\Delta_{xy}T$ can be described as the following expression (2), wherein "α" is a thermal diffusivity of the material. The right side of the expression (2) represents a heat migration balance in the z direction (steel sheet thickness direction) which governs heat migration in the surface layer of the steel sheet 100. That is, the first term of the right side of expression (2) represents a variation of heat storage in the surface layer of the steel sheet and the second term represents a variation of heat storage due to heat migration in the z direction.

$$\Delta_{xy}T = (1/\alpha) \cdot (\partial T/\partial t) - \partial^2 T/\partial z^2 \quad (2)$$

Figure 6A:
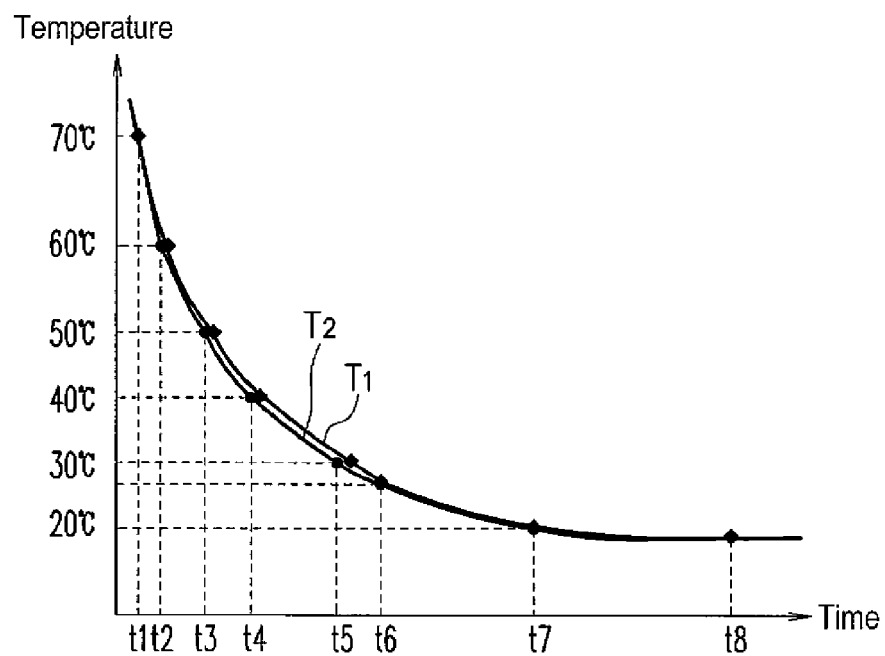
FIGS. 6A/6B are a graph showing temperature characteristics curves representing surface temperature based on thermal image data in a cooling-down/being-heated-up process obtained by an infrared thermography camera.

A case, where temperature characteristics curves $T_1$ and $T_2$ are obtained as shown in FIG. 6A based on thermal image data of the inspection area taken by the infrared thermography camera during cooling down process, is described below. A pixel size by the infrared thermography camera is set at 0.4 mm which is about two times the size of defect 101.

Figure 7A:
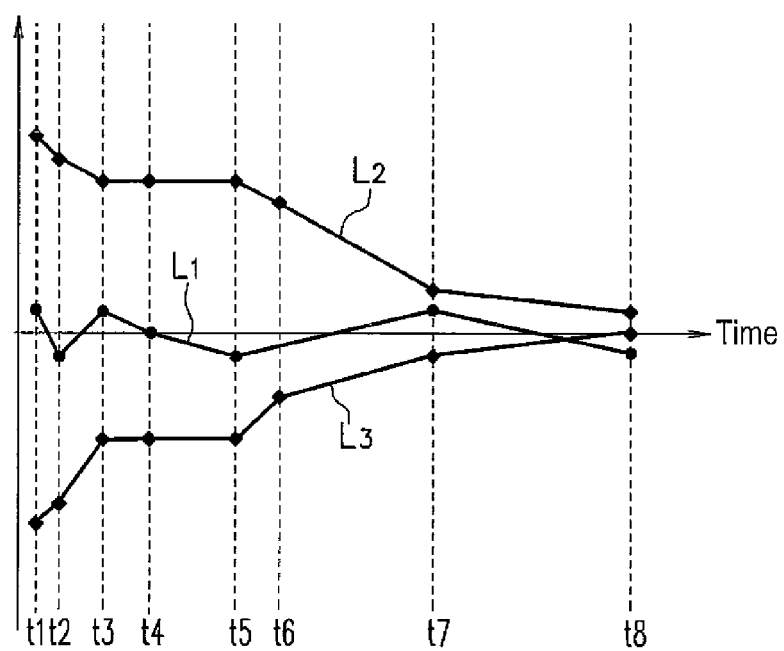
FIGS. 7A/7B are a graph showing Laplacian corresponding to temperature characteristics curves of FIGS. 6A/6B.

The temperature characteristics curve $T_1$ represents temperature characteristics of a normal portion 102 in FIG. 1A and Laplacian $\Delta_{xy}T$ with the $T_1$ being shown in FIG. 7A as characteristics line $L_1$. The characteristics line $L_1$ (Laplacian $\Delta_{xy}T$) indicates the value is almost zero with some deviation by noise. This zero value of Laplacian $\Delta_{xy}T$ means that the value of the first term of the right side of the expression (2) representing a variation of heat storage in the surface layer of the steel sheet (negative value due to the process of being cooled down) is almost equal to the value of the second term of the right side of the expression (2) representing a variation of heat storage due to heat migration in the z direction (negative value due to the process of being cooled down). In other words, the heat migration is being made very smooth.

Figure 8:
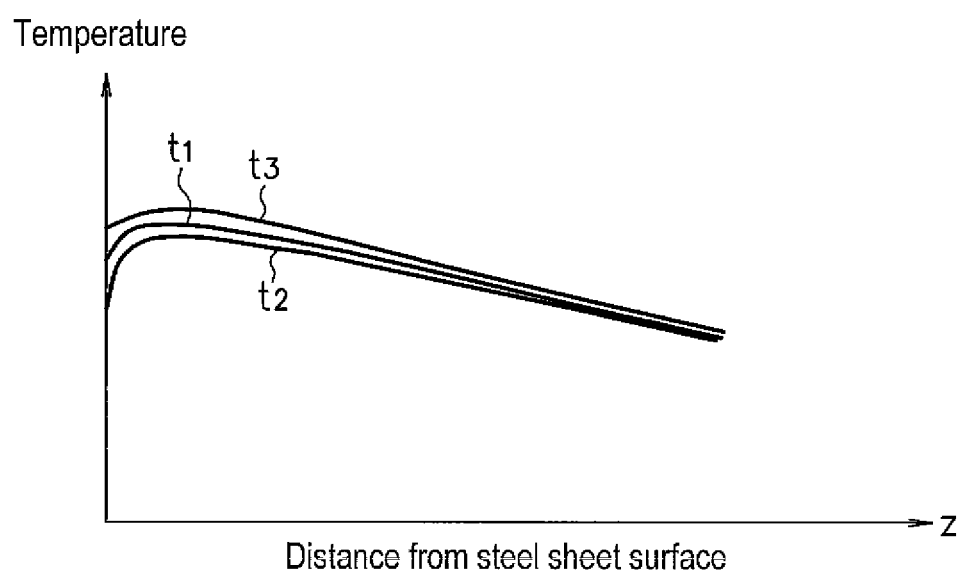
FIG. 8 is a graph showing temperature distribution curves in the surface layer.

The temperature characteristics curve $T_2$ represents temperature characteristics of a position of defect type shown in FIG. 3A and Laplacian $\Delta_{xy}T$ with the $T_2$ being shown in FIG. 7A as characteristics line $L_2$. In the case of the defect type shown in FIG. 3A, a value of the characteristics line $L_2$ (Laplacian $\Delta_{xy}T$) is positive. This positive value of Laplacian $\Delta_{xy}T$ means that the value of the second term of the right side of the expression (2) representing a variation of heat storage due to heat migration in the z direction (negative value due to the process of being cooled down) is smaller than the value of the first term of the right side of the expression (2) representing a variation of heat storage in the surface layer (negative value due to the process of being cooled down). In other words, the cooling down process keeps going while a heat release from the surface of the steel sheet is keeping larger than a heat fed from a deeper place of the steel sheet. This means that a cooling down rate in the defect position is greater than that of the area surrounding the defect as indicated in FIG. 8 where the temperature distribution curve $t_2$ in the surface layer of the defect portion has a convex curve which has a larger gradient compared with the temperature distribution curve $t_1$ in the surface layer of a normal portion. The defect type shown in FIG. 3B has a similar result to that of the defect type of FIG. 3A.

Laplacian $\Delta_{xy}T$ with respect to temperature characteristics curves in a position of defect type shown in FIG. 3C or FIG. 3D is shown in FIG. 7A as characteristics line $L_3$. The temperature characteristics curve representing temperature characteristics of a position of the defect type shown in FIG. 3C or FIG. 3D (not shown in FIG. 6A) is almost the same as the temperature characteristics curves $T_1$ representing temperature characteristics of a normal portion in FIG. 6A. In the case of the defect type shown in FIG. 3C or FIG. 3D, a value of the characteristics line $L_3$ (Laplacian $\Delta_{xy}T$) becomes negative. This negative value of Laplacian $\Delta_{xy}T$ means that the value of the first term of the right side of the expression (2) representing a variation of heat storage in the surface layer (negative value due to the process of being cooled down) is smaller than the value of the second term representing a variation of heat storage due to heat migration in the z direction (negative value due to the process of being cooled down), which results in the temperature distribution curve $t_3$ in the surface layer shown in FIG. 8. The reason for this is because an amount of heat radiation at the defect position is greater than that of the area surrounding the defect, which makes a temperature by an infrared thermography camera show a higher value than actual temperature.

Figure 1D:
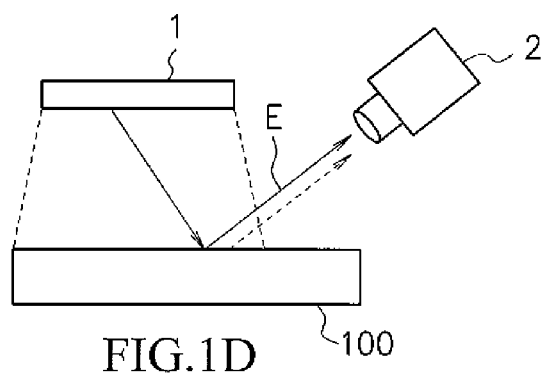
FIG. 1D shows a system for detecting defects while a steel sheet is being heated up.

FIG. 1C and FIG. 1D is a system suitable for detecting defects while a steel sheet is being heated up. In FIG. 1C, an infrared thermography camera 2 takes an image of an inspection area S where the surface is being heated up by a heating device 1 to obtain two-dimensional thermal image data of the inspection area S.

As described before, in the case where defect detecting is made while a steel sheet is heated up (described later), also a variety of directions and locations can be used, as long as the heating device 1 and the thermography camera 2 are arranged so that the thermal energy emitted by the heating device 1 can come into the camera after being reflected by the surface of the steel sheet.

Figure 6B:
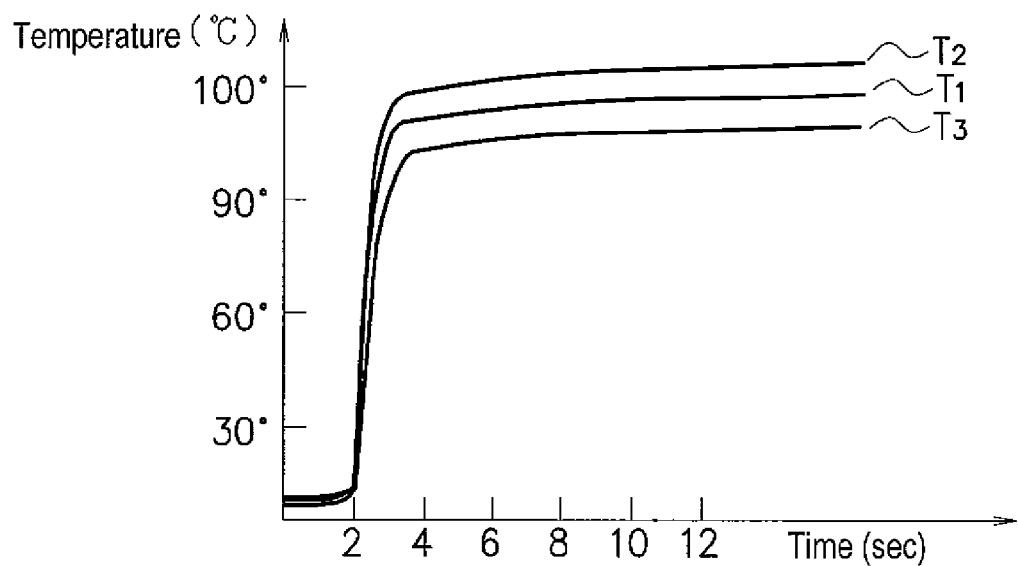

A case, where temperature characteristics curves $T_1$, $T_2$ and $T_3$ are obtained as shown in FIG. 6B based on thermal image data of the inspection area taken by the infrared thermography camera during the heating up process, is described below. In FIG. 6B, the temperature rises steeply and some of the temperature characteristics curves reaches temperature beyond the preferable temperature range of the steel sheet 100 (less than 100° C.). However, this is just because thermal energy radiated from the heating device 1 comes into the camera after being reflected by the surface of the steel sheet as shown in FIG. 1D.

Figure 7B:
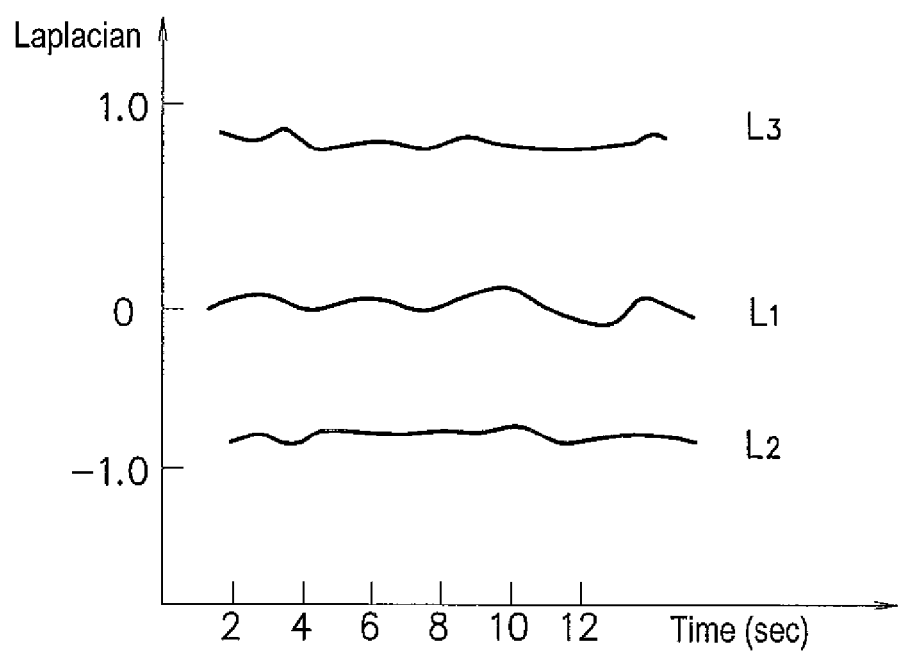

The temperature characteristics curve $T_1$ represents temperature characteristics of a normal portion 102 in FIG. 1C and Laplacian $\Delta_{xy}T$ with the $T_1$ being shown in FIG. 7B as characteristics line $L_1$. The characteristics line $L_1$ (Laplacian $\Delta_{xy}T$) indicates the value is almost zero with some hunting by white noise. This zero value of Laplacian $\Delta_{xy}T$ means that the value of the first term of the right side of the expression (2) representing a variation of heat storage in the surface layer of the steel sheet (positive value due to the process of being heated up) is almost equal to the value of the second term of the right side of the expression (2) representing a variation of heat storage due to heat migration in the z direction (positive value due to the process of being heated up). In other words, the heat migration is being made very smooth.

The temperature characteristics curve $T_2$ represents temperature characteristics of a position of the defect type shown in FIG. 3A or FIG. 3B and Laplacian $\Delta_{xy}T$ with the $T_2$ being shown in FIG. 7B as characteristics line $L_2$. In the case of the defect type shown in FIG. 3A or FIG. 3B, a value of the characteristics line $L_2$ (Laplacian $\Delta_{xy}T$) is negative since the value of the second term of the right side of the expression (2) representing an amount of heat migration in the z direction (positive value due to the process of being heated up) becomes larger.

The temperature characteristics curve $T_3$ represents temperature characteristics of a position of the defect type shown in FIG. 3C or FIG. 3D and Laplacian $\Delta_{xy}T$ with the $T_3$ being shown in FIG. 7B as characteristics line $L_3$. In the case of the defect type shown in FIG. 3C or FIG. 3D, a value of the characteristics line $L_3$ (Laplacian $\Delta_{xy}T$) is positive since the value of the second term of the right side of the expression (2) representing an amount of heat migration in the z direction (positive value due to the process of being heated up) becomes smaller.

Figure 9:
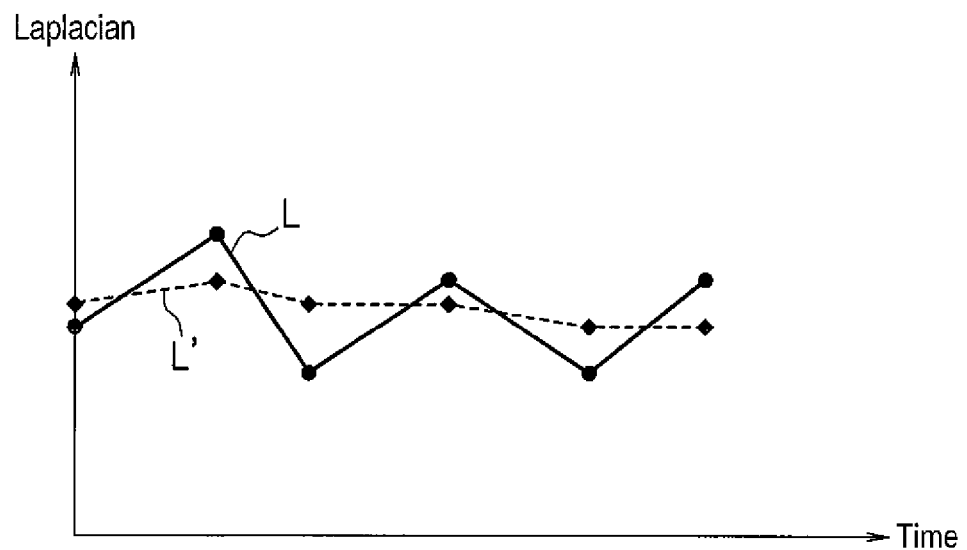
FIG. 9 is a graph showing an effect by Gaussian filtering with respect to thermal image data.

When the thermal image data obtained by the infrared thermography camera 2 includes a noise, Gaussian filtering can be applied to eliminate the noise. FIG. 9 shows characteristics line L as a result of Laplacian processing applied to thermal image data including noise, where Laplacian value greatly hunts because of noise. Another characteristics line L' is a result of Laplacian processing applied to the thermal image data after having a Gaussian filtering process where the hunting is reduced unlike in the line L. As to noise elimination filtering, not only Gaussian filtering but any filtering method for smoothing can be used. As to Gaussian filtering, details are described, for example, in JP2004-219177A.

The following expression (3) represents a thermal energy radiated from a steel sheet surface to be measured by an infrared thermography camera while the steel sheet is in the process of cooling down after being heated up, wherein "$\epsilon$" is a radiation rate of the surface of the steel sheet, "$\epsilon_m$" is an apparent radiation rate set by the user with an infrared thermography camera, T is a temperature of the surface of the steel sheet, "$T_c$" is a temperature of a sensor element of the infrared thermography camera, "$T_m$" is a surface temperature of the steel sheet represented by the infrared thermography camera (surface temperature represented by thermal image data obtained by the infrared thermography camera) and "$\sigma$" is a Stefan-Boltzmann constant.

$$\epsilon \cdot \sigma \cdot (T^4 - T_c^4) = \epsilon_m \cdot \sigma \cdot (T_m - T_c^4) \quad (3)$$

The following expression (4) represents thermal energy radiated from a steel sheet surface to be measured by an infrared thermography camera while the steel sheet is in the process of being heated up, where $T_a$ represents a temperature of the heating element surface of the heating device 1.

$$(1-\epsilon) \cdot \sigma \cdot (T_a^4 - T_c^4) + \epsilon \cdot \sigma \cdot (T^4 - T_c^4) = \epsilon_m \cdot \sigma \cdot (T_m^4 - T_c^4) \quad (4)$$

Comparing the expression (3) with the expression (4), a thermal energy of the first term of the left side is added in the expression (4). This term represents an amount of thermal energy which comes into the sensor of the infrared thermography camera 2 after being emitted from the heating element of the heating device 1 and reflected by the surface (an inspection area S) of the steel sheet 100 (see arrow E in FIG. 1D). $T_a$, a temperature of the heating element surface of the heating device 1, is five times or more T of the surface temperature of the steel sheet 100. Therefore, in the heating up process, the second term of the left side, which is a dominant factor during the cooling down process, is much larger than the first term of the left side in expression (4). This makes it possible to detect a change in the amount of radiation from the surface of the steel sheet 100 with good sensitivity.

As described above, in the method for detecting a defect while the steel sheet is being heated up, a change in the amount of radiation from the surface of the steel sheet 100 can be detected with good sensitivity. Therefore, a defect such as the one shown in FIG. 3B, FIG. 3C or FIG. 3D, particularly the type of FIG. 3C or FIG. 3D, can be detected with good sensitivity. The defect type of FIG. 3A may not be easily detected because the change in the amount of radiation in this type is not so great. That is, the amount of thermal energy of the second term of the left side is expected to be a main change, and the value change of the second term is smaller than the value of the first term.

As described above, the absolute value of the Laplacian $\Delta_{xy}T$, obtained from the surface temperature data based on the thermal image data by the infrared thermography camera, becomes larger at the position of the defect 101 compared with other normal surface portions of the steel sheet. This finding can be used for detecting the defect 101 on the surface or in the surface layer of a steel sheet with high accuracy and without reducing production line speed.

Because of the heat diffusion effect, the area of which temperature is affected by the defect 101 is expanded. This makes it possible to set a pixel size larger compared with an optical defect detecting device using a CCD camera.

Figure 10:
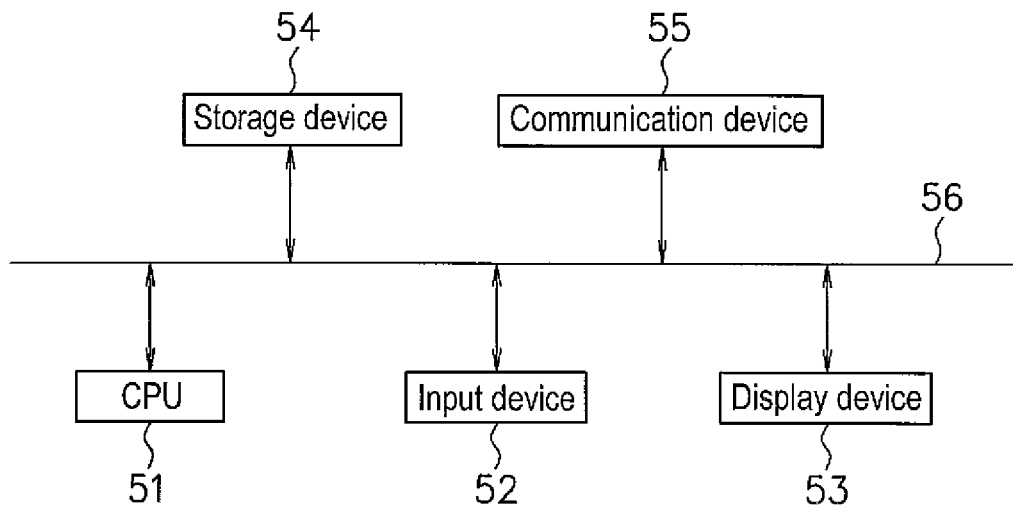
FIG. 10 shows a hardware configuration of a computer system functioning as a detecting device.

FIG. 10 shows a hardware configuration of a computer system functioning as a detecting device 3. The hardware configuration includes CPU 51, input device 52, display device 53, storage device 54 and communication device 55, each of them is connected to each other through bus 56. The storage device 54 includes ROM, RAM, and HD where the computer program for controlling an operation of the detecting device 3 is stored. When CPU 51 executes the program, function and processing by the detecting device 3 can be realized. The detecting device 3 can be constituted by a single unit or a plurality of units.

Examples when detecting defects is made while a steel sheet is being cooled down are shown as follows.

FIG. 11 shows an example where defect detection was made with respect to a steel sheet sample (test piece) having a defect shown as FIG. 3A, i.e., a foreign material or a void located in the surface layer of the steel sheet. Thermal image data of the steel sheet sample was taken by an infrared thermography camera in the cooling down process, i.e., 10 seconds after the steel sheet sample was heated to about 80° C. The number of pixels of the infrared thermography camera is 256×256, the size of the pixel is 0.8 mm, and the distance between the camera and the steel sheet sample was 60 cm. Optical axis direction of the infrared thermography camera is perpendicular to the steel sheet sample surface.

Figure 11A:
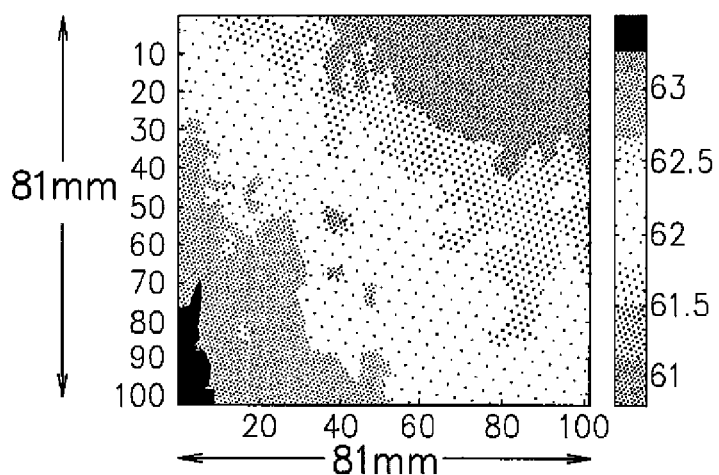
FIGS. 11A, 11B and 11C are an example of an image showing detecting a defect in the cooling down process, wherein the defect is a foreign material or a void located in the surface layer of the steel sheet.
Figure 11B:
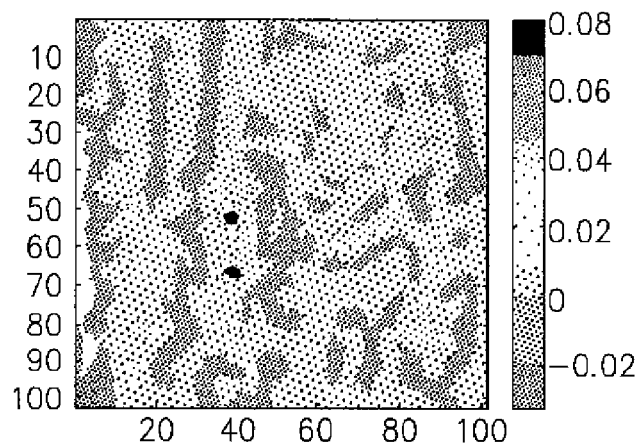
Figure 11C:
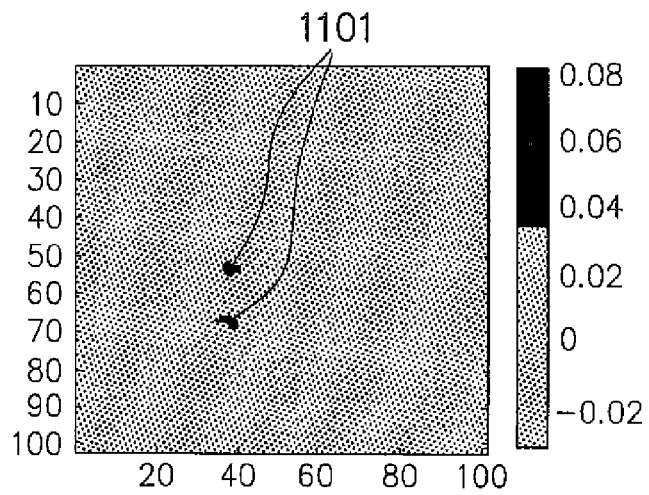

FIG. 11A is thermal image data taken by the infrared thermography camera, FIG. 11B is a Laplacian processed image of the thermal image data, and FIG. 11C is a binarized image of the Laplacian processed image data. FIGS. 11A, 11B and 11C are schematic diagrams made from an actually obtained image (zoom-up image). FIG. 11C shows the image where defects 1101 (a foreign material or a void) are extracted to be clearly viewed.

FIG. 12 shows an example where defect detection was made with respect to a steel sheet sample (test piece) having a defect shown as FIG. 3B, i.e., a minute raised convex portion formed on the surface of the steel sheet. Thermal image data of the steel sheet sample was taken by an infrared thermography camera in the cooling down process, i.e., 10 seconds after the steel sheet sample was heated to about 60° C. The number of pixels of the infrared thermography camera is 256×256, the size of the pixel is 1.2 mm, and the distance between the camera and the steel sheet sample was 90 cm. Optical axis direction of the infrared thermography camera is perpendicular to the steel sheet sample surface.

Figure 12A:
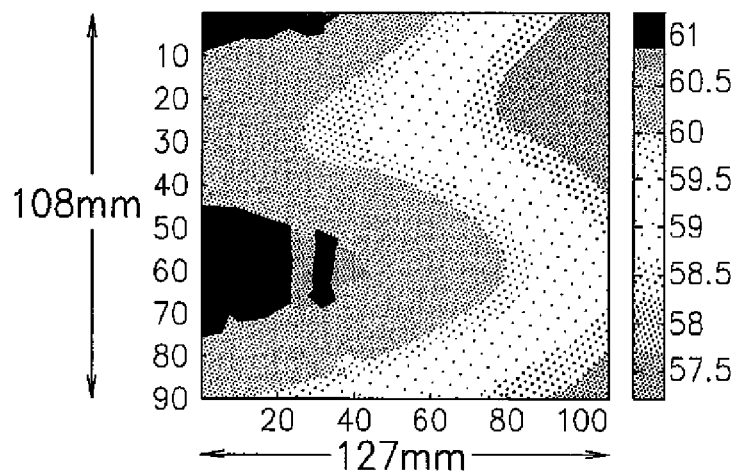
FIGS. 12A, 12B and 12C are an example of an image showing detecting a defect in the cooling down process, wherein the defect is a minute raised convex portion located on the surface of the steel sheet.
Figure 12B:
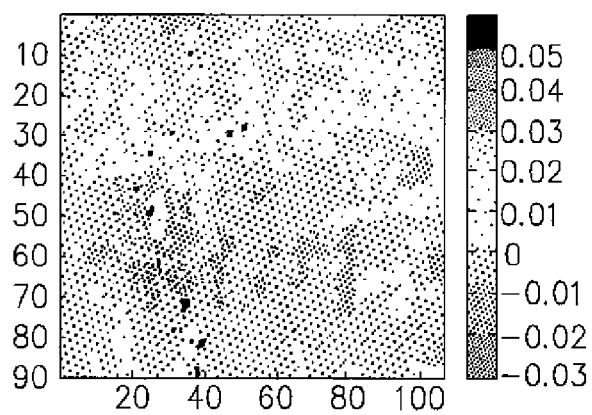
Figure 12C:
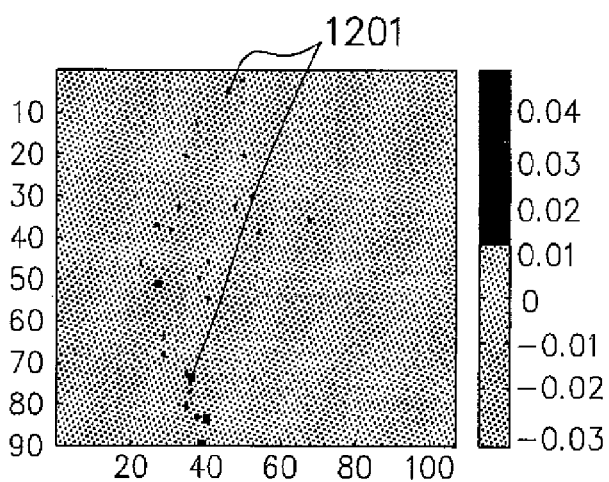

FIG. 12A is thermal image data taken by the infrared thermography camera, FIG. 12B is a Laplacian processed image of the thermal image data, and FIG. 12C is a binarized image of the Laplacian processed image data. FIGS. 12A, 12B and 12C are schematic diagrams made from an actually obtained image (zoom-up image). FIG. 12C shows the image where defects 1201 (a minute raised convex portion) are extracted to be clearly viewed.

FIG. 13 shows an example where defect detection was made with respect to a steel sheet sample (test piece) having a defect shown as FIG. 3C, i.e., a minute sharp dent formed on the surface of the steel sheet. Thermal image data of the steel sheet sample was taken by an infrared thermography camera in the cooling down process, i.e., 10 seconds after the steel sheet sample was heated to about 80° C. The number of pixels of the infrared thermography camera is 256×256, the size of the pixel is 0.1 mm, and the distance between the camera and the steel sheet sample was 10 cm. Optical axis direction of the infrared thermography camera is perpendicular to the steel sheet sample surface.

Figure 13A:
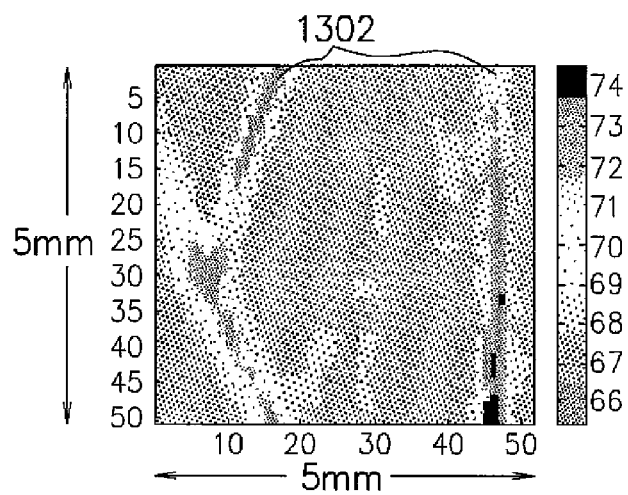
FIGS. 13A, 13B and 13C are an example of an image showing detecting a defect in the cooling down process, wherein the defect is a minute sharp dent located on the surface of the steel sheet.
Figure 13B:
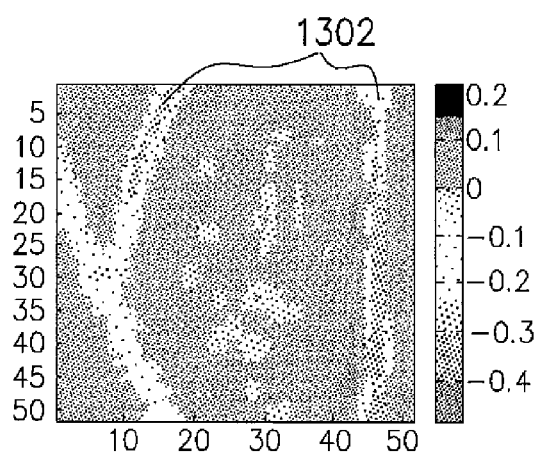
Figure 13C:
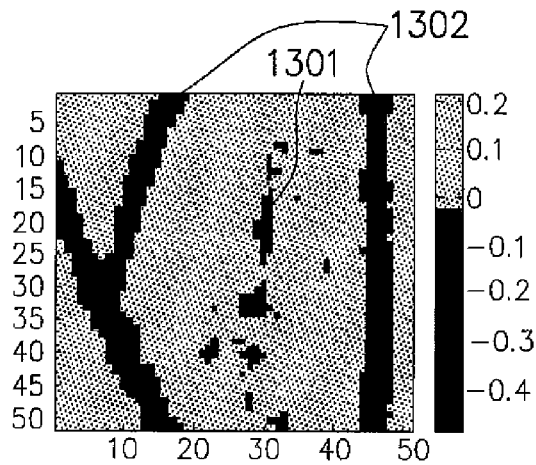

FIG. 13A is thermal image data taken by the infrared thermography camera, FIG. 13B is a Laplacian processed image of the thermal image data, and FIG. 13C is a binarized image of the Laplacian processed image data. FIGS. 13A, 13B and 13C are schematic diagrams made from an actually obtained image (zoom-up image). FIG. 13C shows the image where defects 1301 (a minute sharp dent) are extracted to be clearly viewed. A line pattern 1302 viewed in FIGS. 13A, 13B and 13C is a marking line written on the sample in advance to indicate a portion having the defects after finding the defect by doing a visual check, but not any kind of erroneous detection.

FIG. 14 shows an example where defect detection was made with respect to a steel sheet sample (test piece) having a defect shown as FIG. 3D, i.e., a foreign material such as dust attached on the surface of the steel sheet. Thermal image data of the steel sheet sample was taken by an infrared thermography camera in the cooling down process, i.e., 10 seconds after the steel sheet sample was heated to about 60° C.

The number of pixels of the infrared thermography camera is 256×256, the size of the pixel is 0.8 mm, and the distance between the camera and the steel sheet sample was 60 cm. Optical axis direction of the infrared thermography camera is perpendicular to the steel sheet sample surface.

Figure 14A:
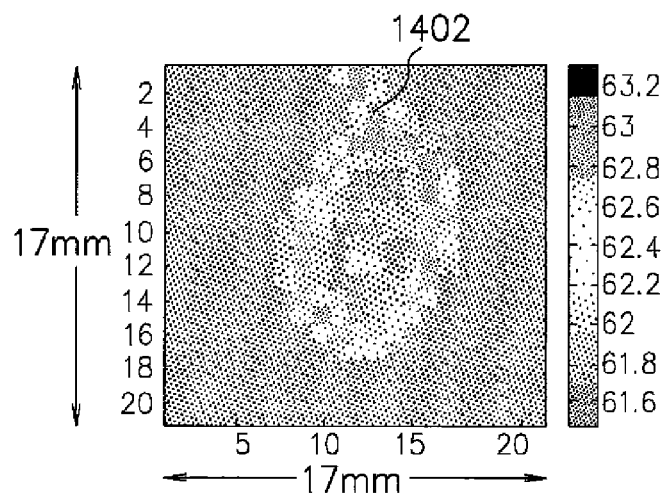
FIGS. 14A, 14B and 14C are an example of an image showing detecting a defect in the cooling down process, wherein the defect is a foreign material attached on the surface of the steel sheet.
Figure 14B:
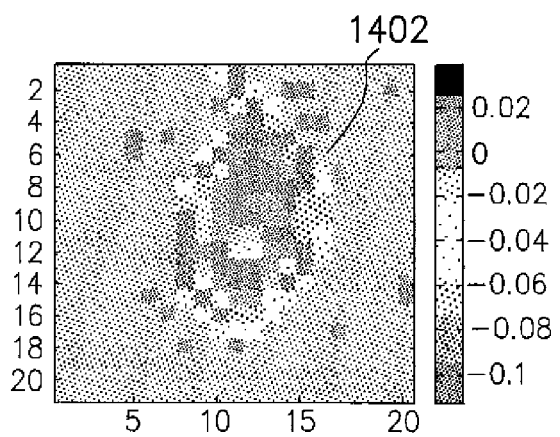
Figure 14C:
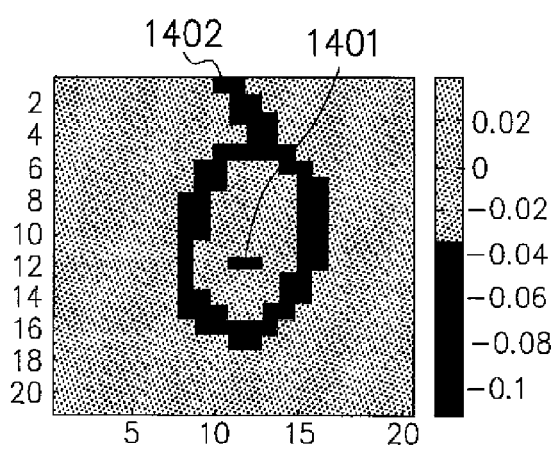

FIG. 14A is thermal image data taken by the infrared thermography camera, FIG. 14B is a Laplacian processed image of the thermal image data, and FIG. 14C is a binarized image of the Laplacian processed image data. FIGS. 14A, 14B and 14C are schematic diagrams made from an actually obtained image (zoom-up image). FIG. 14C shows the image where defects 1401 (a foreign material attached) are extracted to be clearly viewed. A line pattern 1402 viewed in FIGS. 14A, 14B and 14C is a marking line written on the sample in advance to indicate a portion having the defects after finding the defect by doing a visual check, but not any kind of erroneous detection.

This invention can be applied to other type of materials. FIG. 15 shows an example where defect detection was made with respect to a sample of a resin fuel tank for an automobile having a foreign material in the surface layer of the tank shell in place of a steel sheet. Thermal image data of the fuel tank sample was taken by an infrared thermography camera in the cooling down process, i.e., 10 seconds after the fuel tank sample was heated to about 60° C. The number of pixels of the infrared thermography camera is 256×256, the size of the pixel is 0.8 mm, and the distance between the camera and the fuel tank sample was 60 cm. Optical axis direction of the infrared thermography camera is perpendicular to the fuel tank sample surface.

Figure 15A:
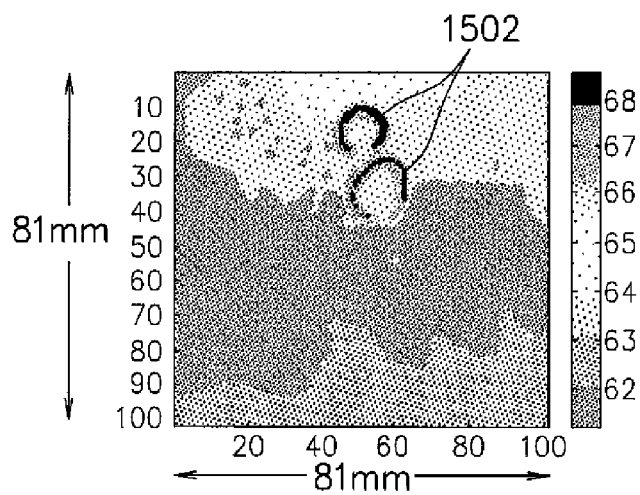
FIGS. 15A, 15B and 15C are an example of an image showing detecting a defect in the cooling down process, wherein the defect is a foreign material in the surface layer of a resin fuel tank for an automobile.
Figure 15B:
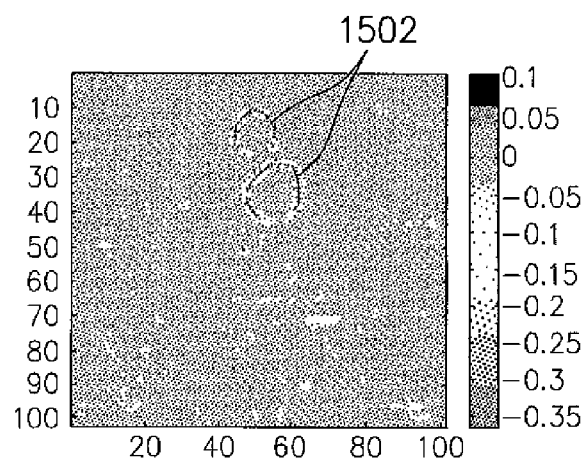
Figure 15C:
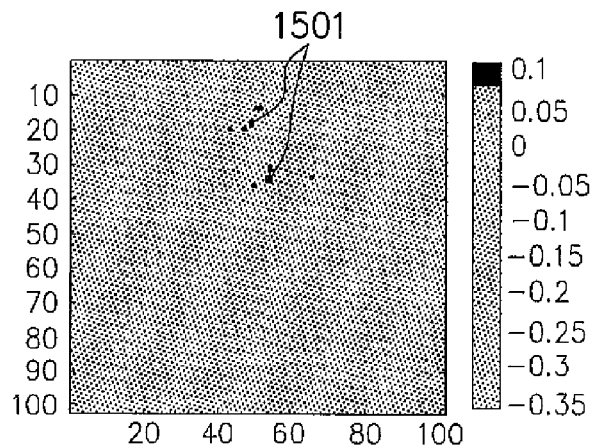

FIG. 15A is thermal image data taken by the infrared thermography camera, FIG. 15B is a Laplacian processed image of the thermal image data, and FIG. 15C is a binarized image of the Laplacian processed image data. FIGS. 15A, 15B and 15C are schematic diagrams made from an actually obtained image (zoom-up image). FIG. 15C shows the image where defects 1501 (a foreign material in the surface layer) are extracted to be clearly viewed. A ring pattern 1502 viewed in FIGS. 15A and 15B is a marking line written on the sample in advance to indicate a portion having the defects after finding the defect by doing a visual check, but not any kind of erroneous detection.

Examples when detecting defects is made while a steel sheet is being heated up are shown as follows.

FIG. 16 shows an example where defect detection was made with respect to a steel sheet sample (test piece) having a defect shown as FIG. 3B, i.e., a minute raised convex portion formed on the surface of the steel sheet. Thermal image data of the steel sheet sample was taken by an infrared thermography camera while the steel sheet sample was being heated up to about 60° C. The number of pixels of the infrared thermography camera is 256×256, the size of the pixel is 0.8 mm, and the distance between the camera and the steel sheet sample was 60 cm. The angle between the heating direction by the heating device and the steel sheet surface is 60°, and the angle between the optical axis direction of the camera and the steel sheet surface is 90°.

Figure 16A:
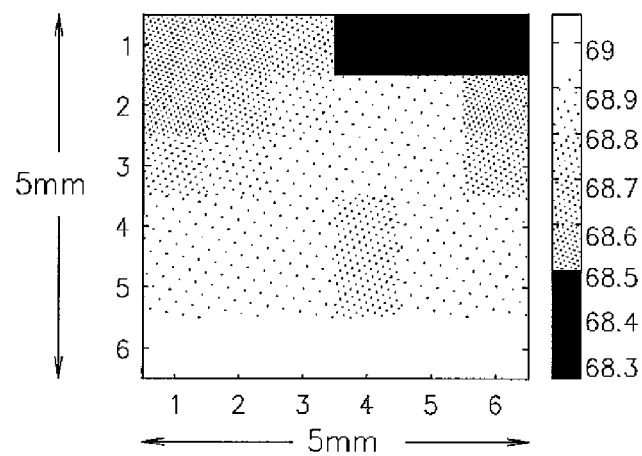
FIGS. 16A, 16B and 16C are an example of an image showing detecting a defect in the heating process, wherein the defect is a minute raised convex portion located on the surface of the steel sheet.
Figure 16B:
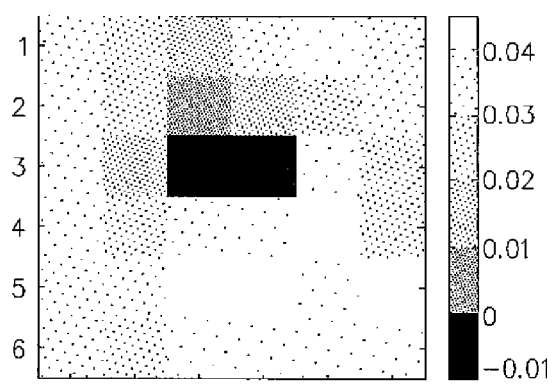
Figure 16C:
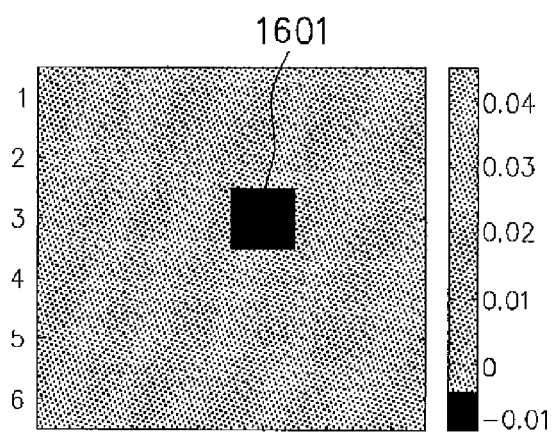

FIG. 16A is thermal image data taken by the infrared thermography camera, FIG. 16B is a Laplacian processed image of the thermal image data, and FIG. 16C is a binarized image of the Laplacian processed image data. FIGS. 16A, 16B and 16C are schematic diagrams made from an actually obtained image (zoom-up image). FIG. 16C shows the image where defects 1601 (a minute raised convex portion) are extracted to be clearly viewed.

FIG. 17 shows an example where defect detection was made with respect to a steel sheet sample (test piece) having a defect shown as FIG. 3C, i.e., a minute sharp dent formed on the surface of the steel sheet. Thermal image data of the steel sheet sample was taken by an infrared thermography camera while the steel sheet sample was being heated up to about 40° C. The number of pixels of the infrared thermography camera is 256×256, the size of the pixel is 0.8 mm, and the distance between the camera and the steel sheet sample was 60 cm. The angle between the heating direction by the heating device and the steel sheet surface is 60°, and the angle between the optical axis direction of the camera and the steel sheet surface is 90°.

Figure 17A:
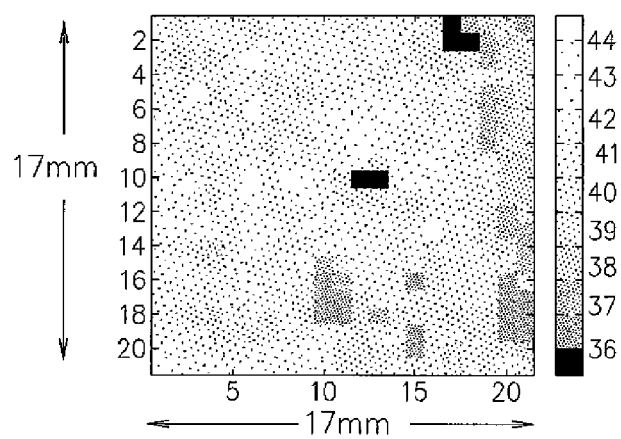
FIGS. 17A, 17B and 17C are an example of an image showing detecting a defect in the heating process, wherein the defect is a minute sharp dent located on the surface of the steel sheet.
Figure 17B:
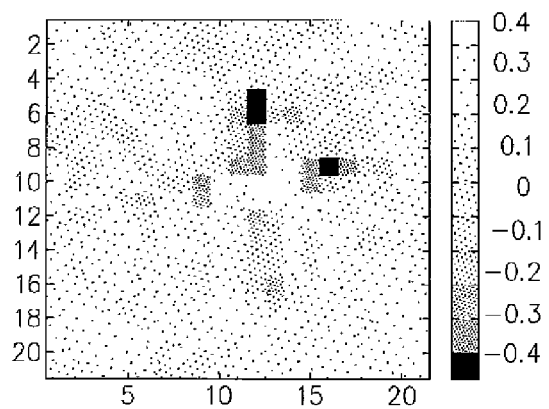
Figure 17C:
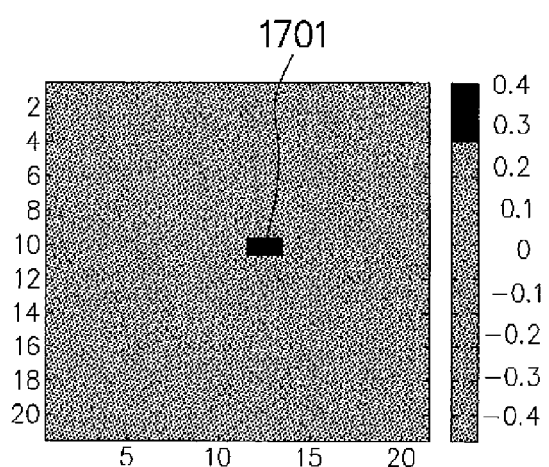

FIG. 17A is thermal image data taken by the infrared thermography camera, FIG. 17B is a Laplacian processed image of the thermal image data, and FIG. 17C is a binarized image of the Laplacian processed image data. FIGS. 17A, 17B and 17C are schematic diagrams made from an actually obtained image (zoom-up image). FIG. 17C shows the image where defects 1701 (a minute sharp dent) are extracted to be clearly viewed.

FIG. 18 shows an example where defect detection was made with respect to a steel sheet sample (test piece) having a defect shown as FIG. 3D, i.e., a foreign material attached to the surface of the steel sheet. Thermal image data of the steel sheet sample was taken by an infrared thermography camera while the steel sheet sample was being heated up to about 90° C. The number of pixels of the infrared thermography camera is 256×256, the size of the pixel is 0.8 mm, and the distance between the camera and the steel sheet sample was 60 cm. The angle between the heating direction by the heating device and the steel sheet surface is 60°, and the angle between the optical axis direction of the camera and the steel sheet surface is 90°.

Figure 18A:
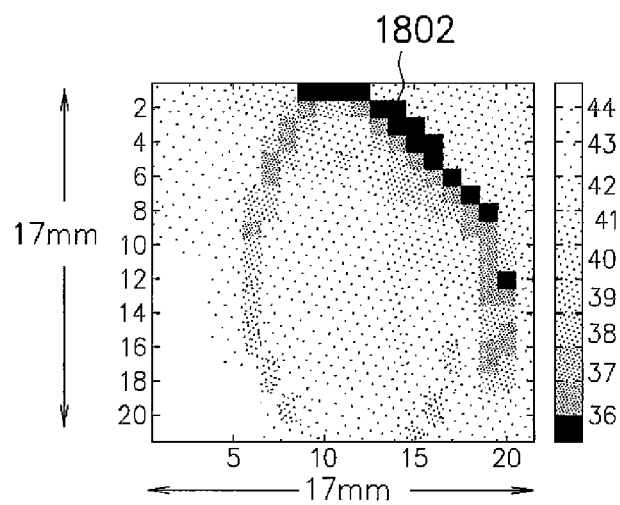
FIGS. 18A, 18B and 18C are an example of an image showing detecting a defect in the heating process, wherein the defect is a foreign material attached on the surface of the steel sheet.
Figure 18B:
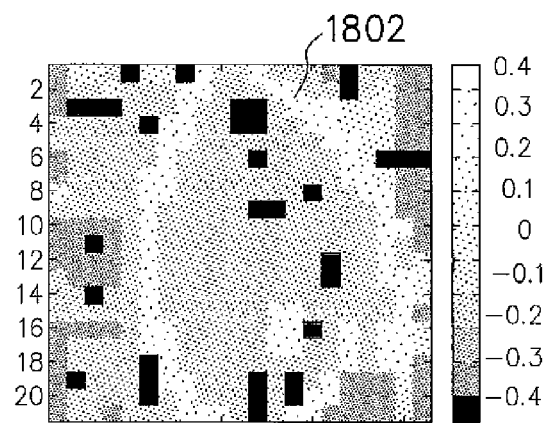
Figure 18C:
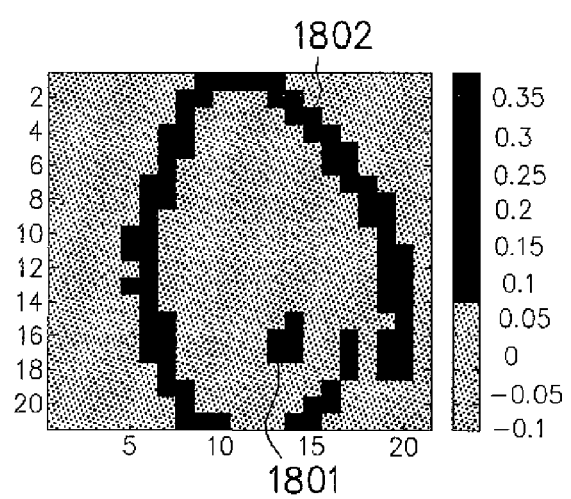

FIG. 18A is thermal image data taken by the infrared thermography camera, FIG. 18B is a Laplacian processed image of the thermal image data, and FIG. 18C is a binarized image of the Laplacian processed image data. FIGS. 18A, 18B and 18C are schematic diagrams made from an actually obtained image (zoom-up image). FIG. 18C shows the image where defects 1801 (a foreign material attached) are extracted to be clearly viewed. A line pattern 1802 viewed in FIGS. 18A, 18B and 18C is a marking line written on the sample in advance to indicate a portion having the defects after finding the defect by doing a visual check, but not any kind of erroneous detection.

This invention can be applied to other types of material. FIG. 19 shows an example where defect detection was made with respect to a sample of a resin fuel tank for an automobile having a foreign material in the surface layer of the tank shell in place of the steel sheet. Thermal image data of the fuel tank sample was taken by an infrared thermography camera while the fuel tank sample was being heated up to about 70° C. The number of pixels of the infrared thermography camera is 256×256, the size of the pixel is 0.8 mm, and the distance between the camera and the fuel tank sample was 60 cm. The angle between the heating direction by the heating device and the fuel tank surface is 60°, and the angle between the optical axis direction of the camera and the fuel tank surface is 90°.

Figure 19A:
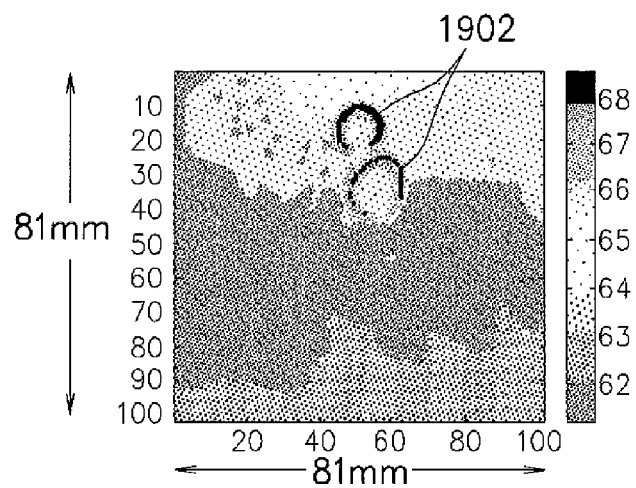
FIGS. 19A, 19B and 19C are an example of an image showing detecting a defect in the heating process, wherein the defect is a foreign material in the surface layer of a resin fuel tank for an automobile.
Figure 19B:
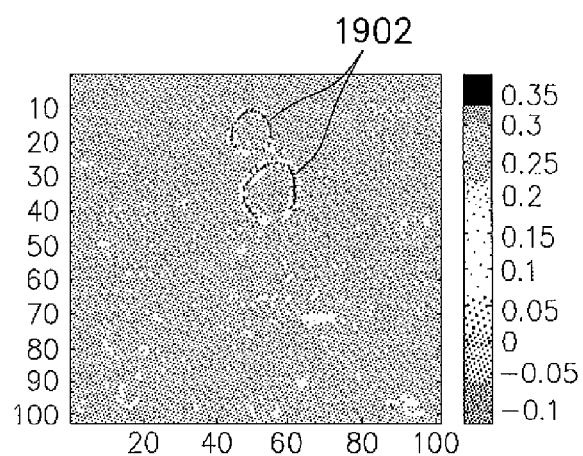
Figure 19C:
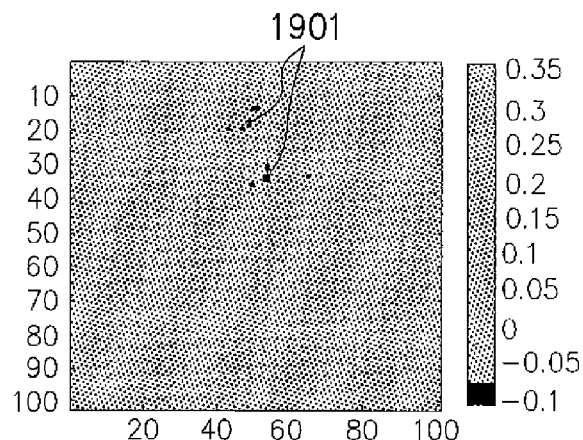

FIG. 19A is thermal image data taken by the infrared thermography camera, FIG. 19B is a Laplacian processed image of the thermal image data, and FIG. 19C is a binarized image of the Laplacian processed image data. FIGS. 19A, 19B and 19C are schematic diagrams made from an actually obtained image (zoom-up image). FIG. 19C shows the image where defects 1901 (a foreign material in the surface layer) are extracted to be clearly viewed. A ring pattern 1902 viewed in FIGS. 19A and 19B is a marking line written on the sample in advance to indicate a portion having the defects after finding the defect by doing a visual check, but not any kind of erroneous detection.

The present invention is based on finding a singular point of heat transfer phenomenon on the surface or in the surface layer of the material. Heat transfer phenomenon can take place in any material and any shape of defect on the surface or in the surface layer can be detected by a thermography camera, which makes it possible to apply the invention to any material in addition to a steel sheet and resin material.

Although, in the examples represented by FIGS. 11, 12, 13, 14 and 15, the defect detection was made while the steel sheet or the fuel tank was stayed in the same place, as previously described, the defect detection can be made on a moving steel sheet or transported fuel tank. For example, in a commercially available infrared thermography camera, the integration time is in the order of 0.01 ms. This means there is only 0.025 mm of slippage when the steel sheet runs at 150 mpm, which leads to only 10% or less with respect to a pixel having a size of 0.25 mm or more. In other words, the quality of the image is almost not degraded.

What is claimed is:

1. A method for detecting a defect both on the surface and in the surface layer of a material, comprising the steps of:
   making a temperature of the surface of the material be changed with time,
   obtaining thermal image data of the surface of the material using an infrared thermography camera while the surface of the material is changing in temperature, and
   detecting the defect by calculating Laplacian $\Delta_{xy}T$ shown in the right side of the following expression (1) using the following expression (2), where Laplacian $\Delta_{xy}T$ represents a variation of heat storage due to heat migration in a sheet thickness direction z of the material, by using a thermal diffusivity $\alpha$ of the material as shown in the left side of the following expression (1), based on the obtained thermal image data T:

$$(1/a) \cdot (\partial T/\partial t) - \partial^2 T/\partial z^2 = \Delta_{xy}T \qquad (1)$$

$$\Delta_{xy}T = \frac{1}{4h^2}\{T(x+1,y) + T(x-1,y) + T(x,y+1) + T(x,y-1) - 4T(x,y)\}. \qquad (2)$$

2. A method for detecting a defect both on the surface and in the surface layer of a material, comprising the steps of:
   heating the surface of the material,
   obtaining thermal image data of the surface of the material using an infrared thermography camera while the surface of the material is being cooled down after the heating step, and
   detecting the defect by calculating Laplacian $\Delta_{xy}T$ shown in the right side of the following expression (1) using the following expression (2), where Laplacian $\Delta_{xy}T$ represents a variation of heat storage due to heat migration in a sheet thickness direction z of the material, by using a thermal diffusivity $\alpha$ of the material as shown in the left side of the following expression (1), based on the obtained thermal image data T:

$$(1/a) \cdot (\partial T/\partial t) - \partial^2 T/\partial z^2 = \Delta_{xy}T \qquad (1)$$

$$\Delta_{xy}T = \frac{1}{4h^2}\{T(x+1,y) + T(x-1,y) + T(x,y+1) + T(x,y-1) - 4T(x,y)\}. \qquad (2)$$

3. A method for detecting a defect both on the surface and in the surface layer of a material, comprising the steps of:
   heating the surface of the material,
   obtaining thermal image data of the surface of the material using an infrared thermography camera while the surface of the material is being heated up at the heating step, and
   detecting the defect by calculating Laplacian $\Delta_{xy}T$ shown in the right side of the following expression (1) using the following expression (2), where Laplacian $\Delta_{xy}T$ represents a variation of heat storage due to heat migration in a sheet thickness direction z of the material, by using a thermal diffusivity $\alpha$ of the material as shown in the left side of the following expression (1), based on the obtained thermal image data T:

$$(1/a) \cdot (\partial T/\partial t) - \partial^2 T/\partial z^2 = \Delta_{xy}T \qquad (1)$$

$$\Delta_{xy}T = \frac{1}{4h^2}\{T(x+1,y) + T(x-1,y) + T(x,y+1) + T(x,y-1) - 4T(x,y)\}. \qquad (2)$$

4. The method according to claim 1, wherein the detecting step further includes calculation of the absolute value of the calculated Laplacian to determine whether there is a defect.

5. The method according to claim 1, wherein the step further includes calculation of value of the calculated Laplacian to determine whether the value is positive or negative to determine a type of defect.

6. A system for detecting a defect both on the surface and in the surface layer of a material comprising:
   a temperature changing device for changing a temperature of the surface of the material,
   an infrared thermography camera for obtaining thermal image data of the surface of the material while the surface of the material is changing in temperature, and
   a detecting device for detecting the defect by calculating Laplacian $\Delta_{xy}T$ shown in the right side of the following expression (1) using the following expression (2), where Laplacian $\Delta_{xy}T$ represents a variation of heat storage due to heat migration in a sheet thickness direction z of the material, by using a thermal diffusivity $\alpha$ of the material shown in the left side of the following expression (1), based on the obtained thermal image data T:

$$(1/a) \cdot (\partial T / \partial t) - \partial^2 T / \partial z^2 = \Delta_{xy} T \qquad (1)$$

$$\Delta_{xy} T = \qquad (2)$$
$$\frac{1}{4h^2} \{T(x+1, y) + T(x-1, y) + T(x, y+1) + T(x, y-1) - 4T(x, y)\}.$$

7. A system for detecting a defect both on the surface and in the surface layer of a material comprising:
- a heating device for heating the surface of the material,
- an infrared thermography camera for obtaining thermal image data of the surface of the material while the surface of the material is being cooled down, and
- a detecting device for detecting the defect by calculating Laplacian $\Delta_{xy}T$ shown in the right side of the following expression (1) using the following expression (2), where Laplacian $\Delta_{xy}T$ represents a variation of heat storage due to heat migration in a sheet thickness direction z of the material, by using a thermal diffusivity α of the material as shown in the left side of the following expression (1), based on the obtained image data T:

$$(1/a) \cdot (\partial T / \partial t) - \partial^2 T / \partial z^2 = \Delta_{xy} T \qquad (1)$$

$$\Delta_{xy} T = \qquad (2)$$
$$\frac{1}{4h^2} \{T(x+1, y) + T(x-1, y) + T(x, y+1) + T(x, y-1) - 4T(x, y)\}.$$

8. A system for detecting a defect both on the surface and in the surface layer of a material comprising:
- a heating device for heating the surface of the material,
- an infrared thermography camera for obtaining thermal image data of the surface of the material while the surface of the material is being heated up, and
- a detecting device for detecting the defect by calculating Laplacian $\Delta_{xy}T$ shown in the right side of the following expression (1) using the following expression (2), where Laplacian $\Delta_{xy}T$ represents a variation heat storage due to heat migration in a sheet thickness material, by using a thermal diffusivity α of the material as shown in the left side of the following expression (1), based on the obtained thermal image data T:

$$(1/a) \cdot (\partial T / \partial t) - \partial^2 T / \partial z^2 = \Delta_{xy} T \qquad (1)$$

$$\Delta_{xy} T = \qquad (2)$$
$$\frac{1}{4h^2} \{T(x+1, y) + T(x-1, y) + T(x, y+1) + T(x, y-1) - 4T(x, y)\}.$$

9. The system according to claim 7, wherein the heating device and the infrared thermography camera are arranged so that thermal energy emitted from the heating device is prevented from coming into the infrared thermography camera.

10. The system according to claim 7, wherein a heat shielding member is placed between the heating device and the infrared thermography camera so that thermal energy emitted from the heating device is prevented from coming into the infrared thermography camera.

11. The system according to claim 8, wherein the heating device and the infrared thermography camera are arranged so that thermal energy emitted from the heating device is reflected by the surface of the material to come into the infrared thermography camera.

12. The method according to claim 2, wherein the detecting step further includes calculation of the absolute value of the calculated Laplacian to determine whether there is a defect.

13. The method according to claim 3, wherein the detecting step further includes calculation of the absolute value of the calculated Laplacian to determine whether there is a defect.

14. The method according to claim 2, wherein the detecting step further includes calculation of value of the calculated Laplacian to determine whether the value is positive or negative to determine a type of defect.

15. The method according to claim 3, wherein the detecting step further includes calculation of value of the calculated Laplacian to determine whether the value is positive or negative to determine a type of defect.

* * * * *